(12) United States Patent
Dick

(10) Patent No.: US 6,927,843 B2
(45) Date of Patent: Aug. 9, 2005

(54) NON-INVASIVE MEASUREMENT OF SKIN BILIRUBIN LEVEL

(75) Inventor: Jean-Michel Dick, Pierrelaye (FR)

(73) Assignee: Medick S.A., Pierrelaye (FR)

( * ) Notice: Subject to any disclaimer, the term of this patent is extended or adjusted under 35 U.S.C. 154(b) by 435 days.

(21) Appl. No.: 10/203,158

(22) PCT Filed: Mar. 1, 2001

(86) PCT No.: PCT/FR01/00605

§ 371 (c)(1),
(2), (4) Date: Aug. 6, 2002

(87) PCT Pub. No.: WO01/72222

PCT Pub. Date: Oct. 4, 2001

(65) Prior Publication Data

US 2003/0011773 A1 Jan. 16, 2003

(51) Int. Cl.⁷ .......................... G01N 33/48; A61B 5/00
(52) U.S. Cl. .......................... 356/39; 600/306; 600/315
(58) Field of Search .................... 356/39, 394; 600/315, 600/306, 310, 317, 320–323

(56) References Cited

U.S. PATENT DOCUMENTS

| | | |
|---|---|---|
| 4,398,541 A | 8/1983 | Pugliese |
| 5,259,382 A | 11/1993 | Kronberg |
| 5,933,226 A * | 8/1999 | Yamanishi ................... 356/39 |
| 6,129,664 A * | 10/2000 | Macfarlane et al. ........ 600/315 |

FOREIGN PATENT DOCUMENTS

| | | |
|---|---|---|
| DE | 38 27 457 A1 | 6/1989 |
| EP | 0 747 002 A1 | 12/1996 |

\* cited by examiner

*Primary Examiner*—Zandra V. Smith
(74) *Attorney, Agent, or Firm*—Rothwell, Figg, Ernst & Manbeck

(57) ABSTRACT

The invention concerns a method and a device for non-invasive measurement of a tissue and in particular of the skin bilirubin level. The inventive device is characterized in that it comprises: a reading head (1) capable of sending several flashes of various specific wavelengths towards the tissue (2) to be examined and of receiving and measuring in return the reflected light; a calculator, such as a microprocessor, capable of calculating for each wavelength the amount of reflected light and bring it to a value calculated proportionally to a reference value identical for a predetermined wavelength; and a comparator for comparing the calculated value to a table of reference values.

12 Claims, 3 Drawing Sheets

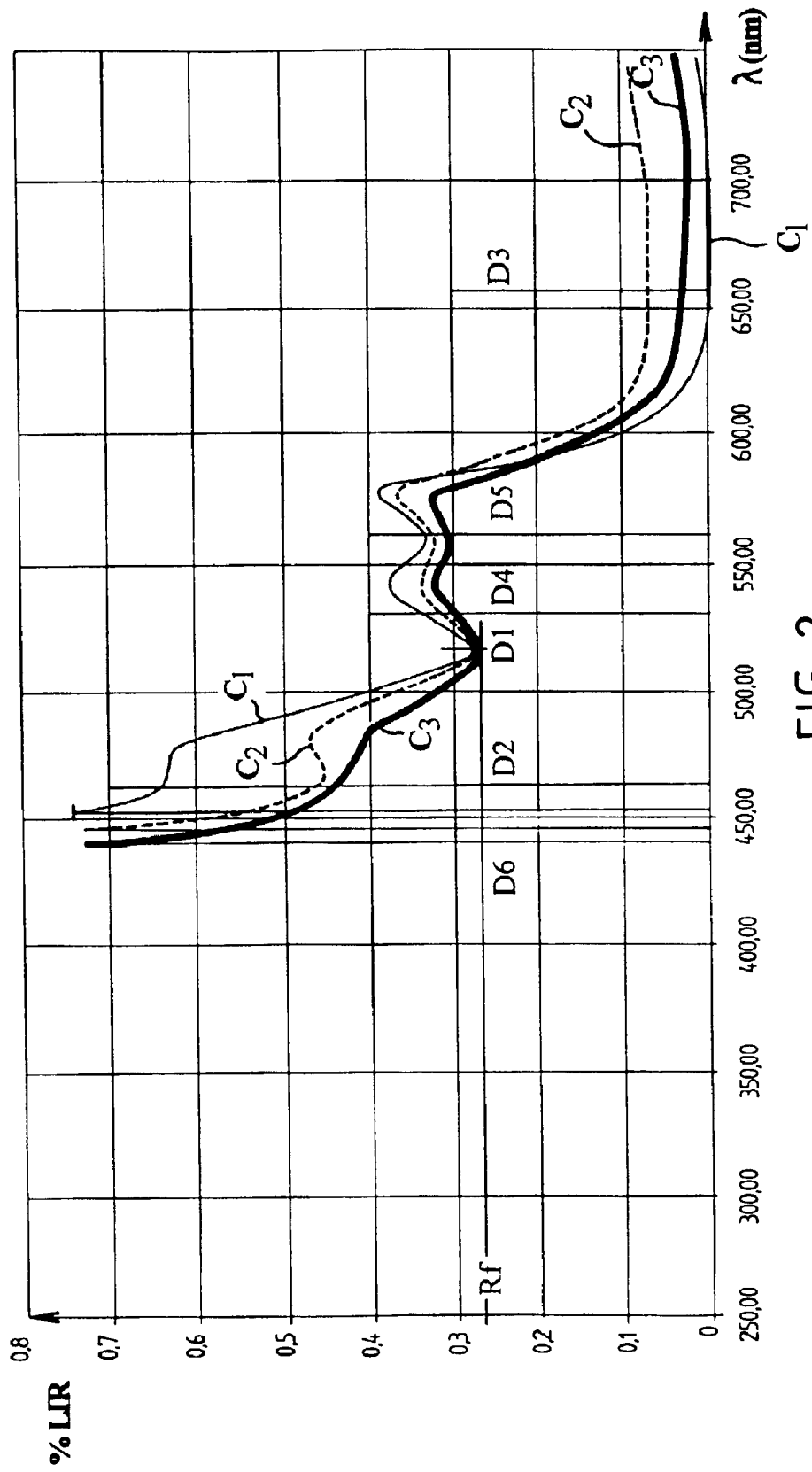
FIG_2

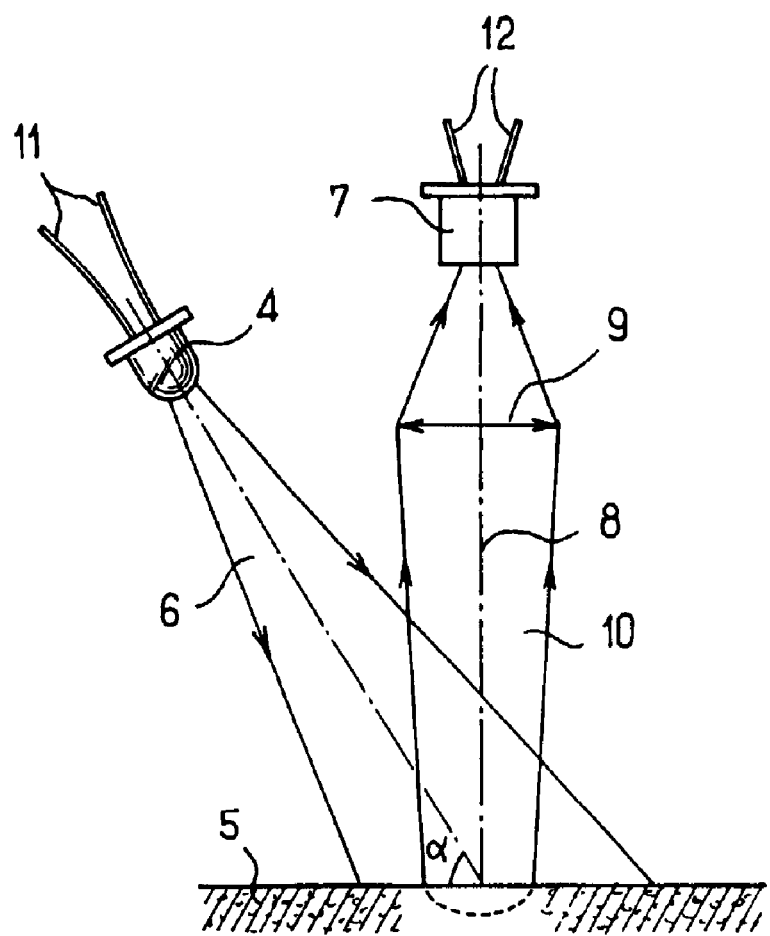
FIG_7

NON-INVASIVE MEASUREMENT OF SKIN BILIRUBIN LEVEL

This invention relates to a process and to a device for the non-invasive analysis of a tissue, such as the skin for instance.

Many works have shown that it was possible, by sending white light on a tissue such as the skin or a plant tissue and analyzing the reflected light, to obtain some information concerning the nature of the tissue and particularly the concentration of its various constituents. The general principle is that the constituents of the various wavelengths that form the white light are reflected differently depending on the constituents encountered by the light. A fine and continuous analysis of the reflected light should thus enable to obtain a fairly precise non-invasive analysis of the tissue being examined.

The devices already known that operate according to this principle require nonetheless a costly optical analysis equipment such as spectrographs and powerful calculators to analyze the collected data, as well as a delicate calibration of the various instruments.

This invention offers a process and a measuring device that overcome these difficulties of implementation.

To this effect, the process of this invention for the measurement of a skin constituent level, particularly that of the bilirubin level in the skin, is characterized in that are performed a first measurement of the reflection of the light with a first given wavelength representative of the measurement to be performed, and at least the measurement of a second reflection of the light of a predetermined wavelength used as reference for which is determined a reflection reference unit value by calculating the ratio k between the reflection measured on the tissue for this second wavelength and the reflection measured on a standard for this same second wavelength; and in that the level of the constituent to be evaluated is deduced by measuring the reflection of the first given wavelength according to a table of predetermined known values for this first wavelength, after correction by the factor k previously measured said reflection measurement so as to obtain the value to be compared with the table of reference values.

A device according to this invention is itself characterized in that it consists of:

a reading head that can send successively several flashes with various defined wavelengths toward the tissue to be examined, and receive and measure in return the reflected light, a calculator such as a microprocessor, that can calculate for each wavelength the quantity of reflected light and bring it to a value calculated proportionally to a reference value identical for a given predetermined reference wavelength, a comparator enabling to compare the value so calculated to a table of reference values.

Advantageously, this device uses electro-luminescent diodes for sending sequential flashes of determined wavelengths.

The invention and its implementation will become more apparent from the following description, together with the accompanying drawings.

In the drawings:

FIG. 2 shows three LIR curves recorded for three subjects, said curves having been subjected to a mathematical treatment so as to level them for a given wavelength threshold.

FIG. 7 is a diagram of a variation in the implementation of a measuring device according to this invention.

Figure 1:
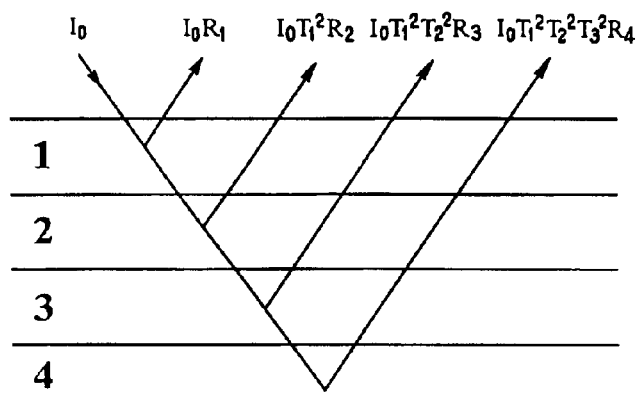
FIG. 1 shows the principle underlying the optical reflection of the light by the skin.

FIG. 1 is a reminder of the principle concerning the propagation of light and of its reflection by the skin. This principle is explicited, in particular, in the publication of Dawson, Barker and al.: "a theoretical and experimental study of the in vivo absorption and diffusion of light by the skin" (Phys. Med. Biol. 1980, vol. 25, n°4, pages 695–709).

Considering successively that the layer 1 is the stratum corneum, that the layer 2 corresponds to the epidermis, that the layer 3 corresponds to the derm and the layer 4 to the hypodermis, if we reference respectively as R1, R2, R3 and R4 the reflection factors of the successive layers and as T1, T2, T3 and T4 the transmission factors of these same layers, the reflected light is globally such as:

$$I = I_o R_1 + I_o T_1^2 R_2 + I_o T_1^2 T_2^2 R_3 + I_o T_1^2 T_2^2 T_3^2 R_4 \ldots$$

If the skin is not too dry, the reflection factors R1, R2 and R3 are notably inferior to R4, while the global reflection is reduced to:

$$R = (I/I_o) \# T_1^2 T_2^2 T_3^2 R_4 \ldots$$

Taking the Neperian logarithm (LN) of the inverse of the reflection, LIR, leads to:

$$LIR = -LN(T_1^2) - LN(T_2^2) - LN(T_3^2) - LN(R_4) \ldots$$

This LIR, represented for all the wavelengths, enables to display all the skin characteristics. It becomes thus possible to draw curves and to deduce from them the skin qualities by analyzing the correspondent absorption bands that characterize the various constituents of the skin, and to deduce for instance the bilirubin, hemoglobin, melanin, etc., levels.

As already mentioned, the practical application of this theory comes up against considerable equipment and calibration difficulties, since the curves vary greatly from one subject to another, depending in particular on the subject's own pigmentation.

With this invention, it becomes nonetheless possible to overcome these difficulties, related to the very different skin reactions from one subject to another, by "tuning" all the curves to the level of a reference threshold for a specific predetermined wavelength $\lambda_f$ used as a reference, which enables to perform a qualitative and quantitative analysis without having to draw the curves (thus avoiding the need for a spectrograph), just by recording a few measurement points for precise and relevant wavelengths, after a simple calculation of threshold setting.

Referring now to FIG. 2, in which were shown three curves with, in ordinate the absorption measured in LIR % as a function of the wavelength of the light received by the skin of three different subjects. Yet, these curves were treated mathematically, in order to standardize them and to show the operation of the device and the process of this invention.

To obtain the curves in FIG. 2, four successive steps are taken.

First step. A calibration is carried out by measuring the reflection on a "gray" or "white" "standard" (e.g. a compacted powder of barium sulfate). For good results, and in particular to eliminate possible drifts in the diodes, as time goes on and/or in response to the room temperature, said calibration/standardization is performed before each measurement on the "gray" or "white" chosen standard.

In the illustrated example, it was assumed that six successive measurements were performed respectively for the wavelengths: 520 nm, 460 nm, 660 nm, 545 nm, 575 nm, and 430 nm. These specific wavelengths can actually be emitted by electro-luminescent diodes DEL of suitable quality.

Figure 3:
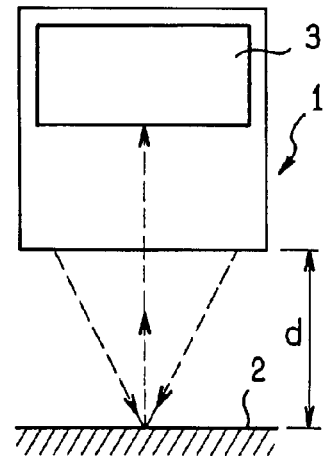
FIG. 3 is a diagram of the principle of a device according to this invention.

FIG. 3 shows a diagram of the measuring device. Here the device 1 comprises electro-luminescent diodes DEL that send a light beam, for example slightly conical and convergent (as shown by the arrows), on the skin 2 of the subject to be examined. The reflected light, essentially perpendicular to the subject's skin, is received by a detector 3 that analyzes the intensity of the radiance received. The use of a conical beam is advantageous on several accounts: it allows for the elimination of most of the specular reflection and also for a precise determination of an optimum distance d between the position of the device 1 and the skin, by measuring the reflection when the light output is essentially reduced to a point on the skin 2. The cone angle is advantageously comprised between 30° and 50°, e.g. around 45°.

The detector of the measuring device records an intensity of the reflection factor:

$I_{OD1}$ for the diode D1,
$I_{OD2}$ for the diode D2, . . .
$I_{OD6}$ for the diode D6.

Second step. An operation is performed to measure the reflection on the skin to be tested.

During the measuring process on the skin of a child "x," the detector of the measuring device records an intensity of the reflection factor:

$I_{xD1}$ for the diode D1,
$I_{xD2}$ for the diode D2, . . .
$I_{xD6}$ for the diode D6.

Third step. Now takes place the mathematical "standardization" treatment so that, for a given reference wavelength, in this case that of the first diode D1 at 520 nm, all the curves go through the same absorption level point, or reflection factor, measured in ordinate.

The calculator, advantageoulsy a microprocessor, performs the following standardization calculations:

$(I_{xD1}/I_{OD1}) = R_{x1}$ for the diode D1

$(I_{xD2}/I_{OD2}) = R_{x2}$ for the diode D2

. . .

$(I_{xD6}/I_{OD6}) = R_{x6}$ for the diode D6

Then the operation is such that, for the reference wavelength selected as relevant $\lambda_{f}$, all the reflection factors $R_{x1f}$ are equal to a reference value Rf.

$R_{x1f} = R_0$ 4 $k = R_0/R_{x1f}$

The various reflection factors $R_{xn}$ are then multiplied by the corresponding factor k to obtain the standardized factors $R_{xnf}$:

$R_{x2f} = k\,R_{x2}$ $R_{x6f} = k\,R_{x6}$

By bringing, for this reference wavelength, all the reflection levels to the same threshold level Rf, it becomes possible to operate a direct reading of the level under examination, for instance the bilirubin level, by simple reading of the corresponding standardized LIR.

Fourth step. From the standardized reflection factors, the microprocessor computes the LIRs:

$LIR_{x1} = Log\,(1/R_{x1f}) = Log\,(1/R_f) = Constant$ $LIR_{x2} = Log\,(1/R_{x2f})$

. . .

$LIR_{x6} = Log\,(1/R_{x6f})$

The LIRs so established enable a comparison with the spectral curves, i.e in the illustrated example three curves corresponding to the various reflection factors of three subjects under examination. In the example of the illustrated curves, the whole curves were actually obtained from a spectrograph analyzing continuously the wavelengths within a range from 430 nm to 750 nm, in order to have a more accurate representation of the path of these curves, though they are not actually necessary for the analysis measurements of the various constituents of the skin, as will be explained in detail thereafter, in reference to the three given examples of measurement.

Back to FIG. 2, for a wavelength of 460 nm, can be found on the three curves respectively C1, C2, C3, corresponding absorption rates of about 0.75, 0.55 and 0.5 measured in % standardized LIR. The simple measurement of said absorption level enables, as can be noted, to deduce that for the subject of the curve C2, the bilirubin level is normal while for the subject of the curve C1, the bilirubin level is high and for the subject of the curve C3, the bilirubin level is too low. These data (these percentages of LIR) can be simply recorded in a table of reference values already tested and known.

Likewise, it is possible to evaluate the hemoglobin content from the reflection rate of the light emitted by the diodes D4 at 545 nm or 550 nm and D5 at 575 nm. Measurements of the reflection level in the emission area of the diode D6 at around 430 nm would add further precision to the results.

The skin pigmentation can be evaluated through the level of the reflection rates vis-à-vis the light emitted by the diode D3 at around 660 nm (within a range from 620 to 780 nm). Actually, it is observed that beyond this, the LIR curve is essentially a straight line, so that the determination on this curve of two points distant enough from this wavelength, e.g. about 620 nm and 780 nm, will enable to determine precisely the corresponding pigmentation characteristic: African, European, Asian, etc. type.

With the process of this invention, it is not necessary to trace the whole curves as it is possible to just resort to limited measurements for wavelengths that are precise and well-defined. This is because the temporary fluctuations and colors or pigmentations specific of the various skins are overcome by the "standardization" process already described.

Moreover, since no mechanical pressure is applied to the tissue to be examined, the measurement is not distorted, as would be the case if the measuring of a skin hemoglobin level were done through a pressure applied to the skin that would drive the blood away from the measurement area.

Thus, when one wants to measure the bilirubin level of the light skin of a quiet baby, this bilirubin level is evaluated directly from the $LIR_{x2}$ measured with the diode D2, by carrying out the operation $LIR_{x2} - LIR_{x1}$.

If the bilirubin level is measured on a colored skin [non-European ethnic group] and/or a restless baby [blood rush in the skin area], the indications for the $LIR_{x2}$ are automatically corrected in the same way because of the subtraction $LIR_{x2} - LIR_{x1}$, and because the value $LIR_{x1}$ was standardized by the operation previously described (same standardized reflection threshold Rf for the diode D1, standardized for each measurement).

Figure 4:
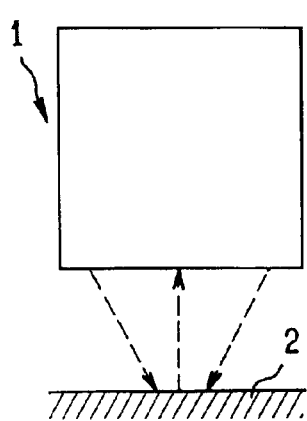
FIGS. 4, 5 and 6 show the principle underlying the practical use of said device.
Figure 5:
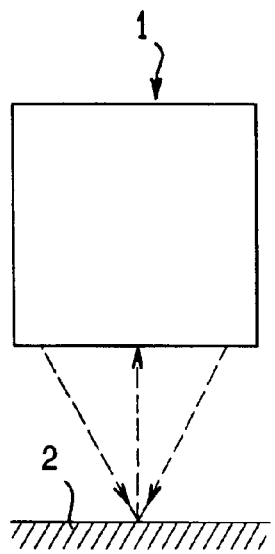
Figure 6:
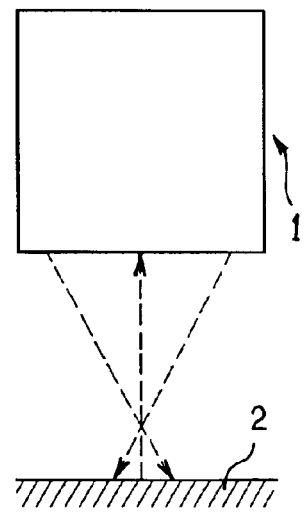

In reference to FIG. 4 to 6 is shown how, because of the use of a conical light beam, it was immediately possible, as shown in FIG. 5, to determine the right measurement distance d between the device and the subject's skin. When the device is too close, as shown in FIG. 4, the skin does not display the pinpoint as in FIG. 5, and neither does it if the device is too far, as shown in FIG. 6.

The device can thus be designed so that, when it is directed toward the skin, the lighting is only triggered when the device is at the right distance, i.e. when the light beam converges essentially into a pinpoint on the skin.

According to the variation of this embodiment shown in FIG. 7, the electro-luminescent diodes DEL with the reading head shown in the diagram 4, light the skin surface shown in 5, from an angle alpha ($\alpha$), advantageouly comprised between 30° and 60°, for instance 45°; the light beam 6 is reflected on the skin; by setting the sensor 7 of the device reading head in the axis 8 perpendicular to the surface 5 of the lit area of the skin, only the part of the light coming from the electro-luminescent diode 4 that is diffused by the skin is detected by the sensor 7, and not the light reflected on the skin surface, which depends on the brightness of the skin. It is thus possible to obtain more reliable data concerning the characteristic to be measured: bilirubin level, hemoglobin level, etc.

In FIG. 7, a lens 9 was brought in the path of the beam 10 of the light diffused by the skin in order to increase the light power detected by the sensor 7. 11 and 12 represent respectively the power wires of the electro-luminescent diodes 4 and of the light output coming from the sensor 7.

Advantageously, if five or six electro-luminescent diodes DEL are used that emit suitable wavelengths such as previously defined, the diodes will preferably be powered successively so that the sensor may successively perform the measurements of the reflection levels needed for the analysis of the results. Prior to each measurement performed on a tissue to be analyzed, the device will have been calibrated, as previously mentioned, upon a "gray" or "standard white", which will allow to calculate the coefficient k such as previously mentioned.

Although the invention was described more precisely for the analysis of the bilirubin level contained in the skin, or other skin constituents such as pigmentation, hemoglobin, etc., the principle of this invention can be extended to the analysis of any tissue, provided that will be determined the precise wavelength(s) for which the reflection level must be recorded to obtain a relevant measurement, and the wavelength on which to tune all the curves so as to obtain the standardization of said curves.

What is claimed is:

1. Process for the measurement of the level of a tissue constituent, characterized in that is/are measured a first light reflection with a first given wavelength that is representative of the measurement to be performed and at least a second measurement of the light reflection for another second predetermined wavelength that will serve as a reference unit value Rf, by calculating the coefficient k between the reflection measured on the tissue for this second wavelength and the reflection measured on a standard for this same second wavelength, and in that the level of the constituent to be evaluated is deduced from the measurement of the reflection of the first wavelength according to a table of predetermined values known for this same first wavelength, after correction by the factor k previously measured of said reflection measurement, so as to obtain the value to be compared to the table reference values, said unit value and said second wavelength determining a point through which will go all the LIR curves after standardization.

2. Process according to claim 1, characterized in that, for an individual's skin, the second wavelength selected is $\lambda$=520 nm.

3. Process according to claim 2, characterized in that, for the measurement of the skin bilirubin level, the wavelength selected is $\lambda$=460 nm.

4. Device for the measurement of the level of a tissue constituent, characterized in that it comprises:

a reading head capable of sending successively several flashes of various predefined wavelengths toward the tissue to be examined as a conical beam having a cone angle between 30° and 50° and of receiving and measuring in return the reflected light, a calculator, capable of calculating for each wavelength the amount of reflected light and of bringing it to a value calculated proportionally to a reference value identical for a predetermined wavelength, a comparator for comparing the calculated value to a table of reference values.

5. Device according to claim 4, characterized in that it comprises electro-luminescent diodes as elements to send successive flashes of various specific wavelengths.

6. Device according to claim 4, characterized in that the light wavelength used to measure the reference value is about 520 nm.

7. Device according to claim 6, characterized in that the light wavelength used to measure the bilirubin level is about 460 nm.

8. Device according to claim 6, characterized in that the light wavelength used to measure the skin pigmentation is comprised between 620 and 780 nm.

9. Device according to claim 6, characterized in that the light wavelength used to measure the skin hemoglobin are two wavelengths or about 545 and 575 nm.

10. Device according to claim 6, characterized in that the light wavelength used to measure the skin hemoglobin is a wavelength of about 550 nm.

11. Device according to claim 6, characterized in that the light wavelength used to measure the skin hemoglobin is a wavelength of about 430 nm.

12. Device according to claim 6, characterized in that the light wavelengths used to measure the skin hemoglobin are two wavelengths of about 550 nm and 430 nm.

* * * * *